US00PP22995P2

(12) United States Plant Patent
Kerley et al.

(10) Patent No.: US PP22,995 P2
(45) Date of Patent: Aug. 28, 2012

(54) ***VIOLA* PLANT NAMED 'KERVIODEEP'**

(50) Latin Name: *Viola×wittrockiana*
Varietal Denomination: Kerviodeep

(76) Inventors: David Kerley, Cambridge (GB); Priscilla Grace Kerley, Cambridge (GB); Timothy Edward Kerley, Cambridge (GB)

( * ) Notice: Subject to any disclaimer, the term of this patent is extended or adjusted under 35 U.S.C. 154(b) by 0 days.

(21) Appl. No.: 13/065,145

(22) Filed: Mar. 14, 2011

(51) Int. Cl.
*A01H 5/00* (2006.01)

(52) U.S. Cl. ..... Plt./323

(58) Field of Classification Search ..... Plt./323
See application file for complete search history.

*Primary Examiner* — Annette Para
(74) *Attorney, Agent, or Firm* — Cassandra Bright

(57) ABSTRACT

A new and distinct *Viola×wittrockiana* cultivar named 'KERVIODEEP' is disclosed, characterized, by a unique combination of a large, round "pansy" type flower, found on a trailing plant. Flower color is a deep red. Plants have a compact, trailing plant habit. The new variety is a *Viola×wittrockiana*, suitable for outdoor landscape and container use.

2 Drawing Sheets

Latin name of the genus and species: *Viola×wittrockiana.*
Variety denomination: 'KERVIODEEP'.

BACKGROUND OF THE INVENTION

The new cultivar is the product of a planned breeding program under the direction of the inventors, David Kerley, Priscilla Kerley and Timothy Kerley, all citizens of the United Kingdom. The objective of the breeding program was to produce new trailing *Viola×wittrockiana* cultivars for commercial ornamental purposes. The new cultivar resulted from the crossing of two unpatented proprietary seedlings. The seed parent was referred to as '05-66-4' and the pollen parent was referred to as '05-66-5'. The cross resulting in 'KERVIODEEP' was performed during May of 2005. The selection of the new variety 'Kerviodeep' was made in April 2006, by the inventors at a research greenhouse located in Cambridge, UK.

Asexual reproduction of the new cultivar 'KERVIODEEP' by vegetative cuttings was first performed at the same research greenhouse in Cambridge, UK in July of 2006, and has shown that the unique features of this cultivar are stable and reproduced true to type in successive generations.

SUMMARY OF THE INVENTION

The cultivar 'KERVIODEEP' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KERVIODEEP' These characteristics in combination distinguish 'KERVIODEEP' as a new and distinct *Viola* cultivar:

1. Unique round "pansy" flower, on a trailing *Viola* plant, rather than the elongated flower form more commonly found on spreading or trailing types which are usually *Viola×williamsii.*
2. Large flower.
3. Spreading, trailing plant habit.

4. Exceptionally compact habit when grown in a small pot.
5. Unique red flower color not found on trailing type *Viola* plants.

PARENT COMPARISON

Plants of the new cultivar 'KERVIODEEP' are similar to plants of the seed parent variety, in most horticultural characteristics. However, plants of the new cultivar produce larger flowers, of a more red color, whereas the seed parent has purple-red flowers. Additionally, the new variety produces flowers with a more round shape.

Plants of the new cultivar 'KERVIODEEP' are similar to plants of the pollen parent variety, in most horticultural characteristics. However, plants of the new cultivar produce larger flowers, of a more red color, whereas the pollen parent has purple-red flowers. Additionally, the new variety produces flowers with a more round shape.

COMMERCIAL COMPARISON

Through reasonable research, the inventors have been unable to identify any similar vegetatively propagated commercial *Viola* varieties, with red flower coloration to compare with 'KERVIODEEP'.

BRIEF DESCRIPTION OF THE PHOTOGRAPHS

Figure 1:
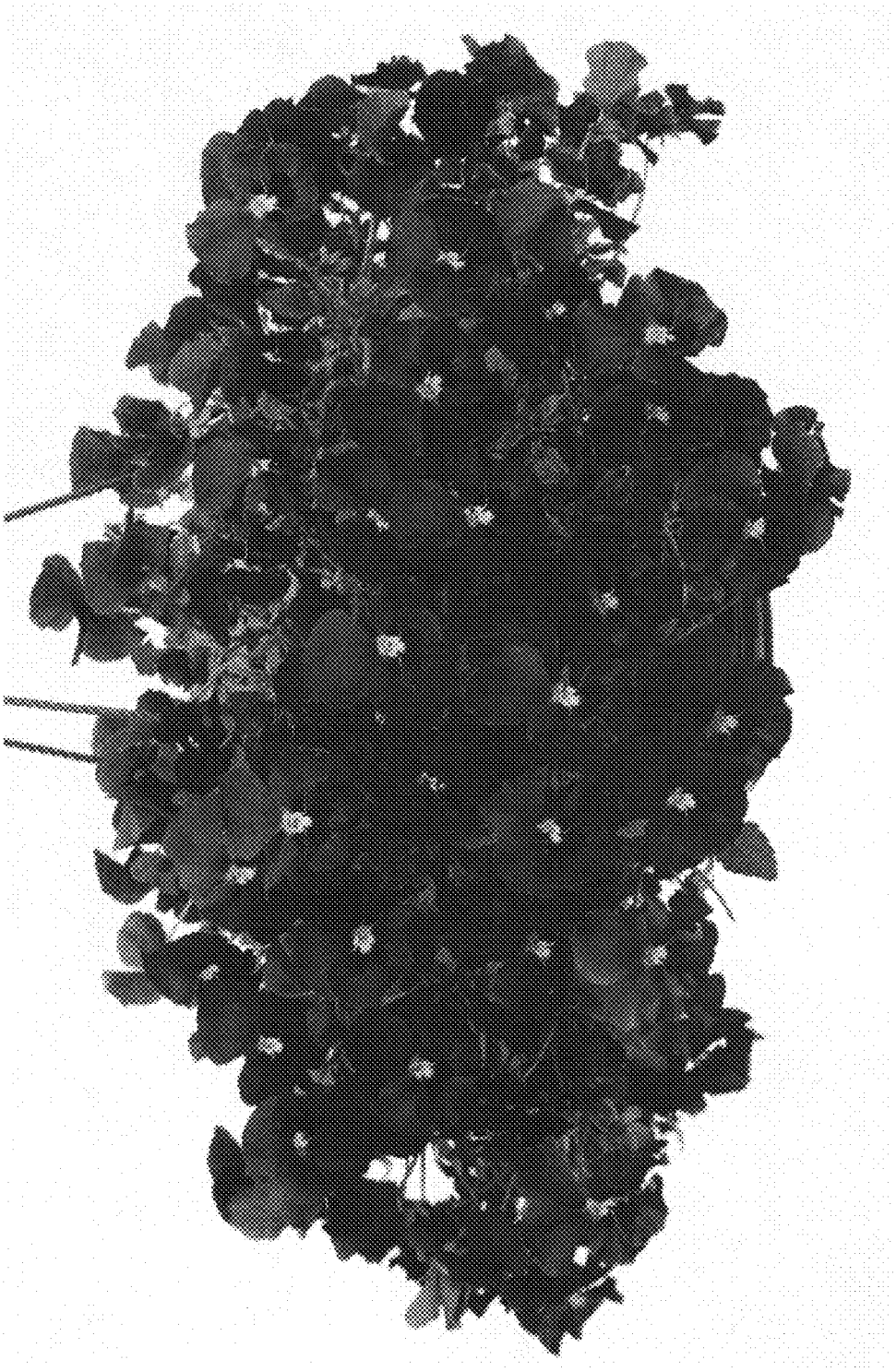

The accompanying photograph in FIG. 1 illustrates in full color typical plants of 'KERVIODEEP' grown in a poly house in Cambridge, UK. Plants are approximately 35 weeks old shown in a 20 cm basket, 3 rooted cuttings were planted per pot.

Figure 2:
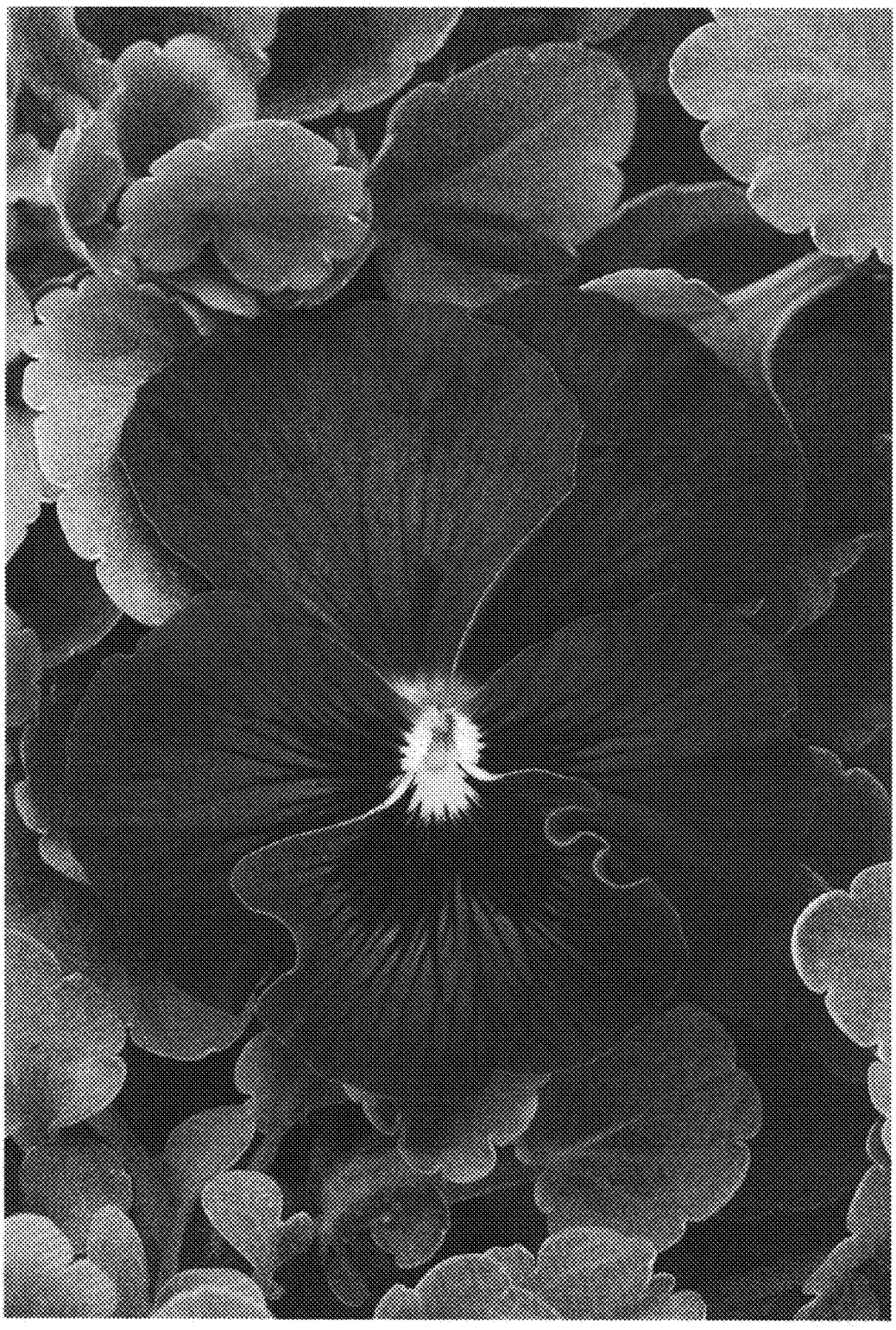

FIG. 2 illustrates a close up of a typical flower of 'KERVOIDEEP'. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 1995 except where general terms of ordinary dictionary significance are used. The following observations and measurements describe 'KERVIODEEP' plants grown in an unheated poly house in Cambridge, UK. The growing temperature ranged from approximately −5 to 12° C. at night to −2 to 18° C. during the day. 3 rooted cuttings were planted in a 20 cm basket. No chemical or photoperiodic treatments were given. Measurements and numerical values represent averages of typical flowering types.

Botanical classification: *Viola×wittrockiana* 'KERVIODEEP'.

Age of the plant described: Approximately 37 weeks, in a 20 cm basket.

PROPAGATION

Time to rooting: About 15 to 20 days at approximately 20° C.

Root description: Fine, fibrous.

PLANT

Growth habit: Spreading, trailing.

Height: Approximately 14 cm.

Plant spread: Approximately 56 cm.

Branching characteristics: Free branching.

Diameter of lateral branches: Approximately 0.5 cm.

Length of lateral branches: Approximately 23 cm.

Texture of lateral branches: Glabrous.

Internode length: Approximately 3.7 cm.

Strength of stem: Strong.

Color of lateral branches: Near RHS Yellow-Green 144, with irregular overlay coloration near Greyed-Purple 187B.

Quantity of lateral and sub lateral branches: Approximately 103.

FOLIAGE

Leaf:

*Arrangement*.—Alternate.

*Average length*.—Approximately 4.2 cm.

*Average width*.—Approximately 2.3 cm.

*Shape of blade*.—Obovate.

*Apex*.—Rounded.

*Base*.—Cordate.

*Attachment*.—Petioled.

*Margin*.—Crenulate.

*Texture of top surface*.—Glabrous.

*Texture of bottom surface*.—Glabrous.

*Color*.—Developing foliage upper side: Near R.H.S. Green 137A. Developing foliage under side: Near R.H.S. Green 137C. Mature foliage upper side: Near R.H.S. Green 139D. Mature foliage under side: Near R.H.S. Green 139D.

*Venation*.—Type: Pinnate. Venation color upper side: Near R.H.S. Green 137A. Venation color under side: Near R.H.S. Green 137C.

Petiole:

*Length*.—3.2 cm.

*Diameter*.—0.2 cm.

*Color*.—Upper surface: Near RHS Yellow-Green 144A.

*Color*.—Lower surface: Near RHS Yellow-Green 144B.

FLOWER

Bloom period: Naturally blooming March to November under United Kingdom outdoor conditions.

Inflorescence:

*Form*.—Single, axillary flowers, comprised of 5 petals total; 2 upper, 2 lateral and 1 lower in a single whorl.

Flower longevity on plant: About 5 days.

Persistent or self-cleaning: Self-Cleaning.

Fragance: Yes, sweet.

Quantity of flower per plant: Approximately 154.

Flower bud:

*Bud color*.—Near RHS Purple 79B, with more red tonality.

*Bud length*.—Approximately 1.9 cm.

*Bud diameter*.—Approximately 0.9 cm.

Individual flower:

*Flower size*.—Length: Approximately 6.3 cm. Width: Approximately 6.1 cm.

*Petal texture*.—All petals, glabrous, velvety with matte appearance.

Petals:

*Upper petals*.—Shape: Orbicular. Length: Approximately 3.5. Width: Approximately 4.2. Margin: Entire. Apex: Rounded. Color: When opening, upper surface: Near RHS Greyed-Purple 187B, with more purple tone. When opening, lower surface: Near RHS Purple 79A, with more red tone. Fully opened, upper surface: Near RHS Red 46A, with over bronze tonality, not identifiable by color chart. Fully opened, lower surface: Near RHS Greyed-Purple 187B with veins Violet 83C. Venation coloration becoming more prominent towards base

*Lateral petals*.—Shape: Broadly reniform. Length: Approximately 3.5 cm. Width: Approximately 3.8 cm. Margin: Entire. Apex: Rounded. Color: When opening, upper surface: More red than 187A; blotch darker than 187A; vein Black 202A, more prominent at base. When opening, lower surface: More purple than 187A. Fully opened, upper surface: deeper and more bronzed than Red 46A; blotch 187B; vein a color between 200A and 202A, more prominent at base. Fully opened, lower surface: Near RHS Greyed-Orange 165A.

*Lower petal*.—Shape: Very broad obocordate to orbicular. Length: Approximately 3.2 cm. Width: Approximately 4.4 cm. Margin: Entire. Apex: Rounded. Color: When opening, upper surface: More red than 187A; blotch Brown 200A; eye Yellow 9A. When opening, lower surface: Near RHS 187B, Green-Yellow 1C at base. Fully opened, upper surface: Deeper and more bronzed than 46A; blotch 187B; eye Yellow 14A. Fully opened, lower surface: Near RHS Greyed-Orange 177B.

Additional flower data:

*Spur on flower petal*.—Length: Approximately 0.6 cm. Width: Approximately 0.2 cm. Depth: Approximately 0.35 cm. Color: Near RHS Violet-Blue 93C, with more grey tone.

*Eye dimensions*.—Length: Approximately 0.6 cm. Width: Approximately 0.4 cm.

Sepals:

*Quantity*.—5.

*Arrangement*.—Whorled.

*Length*.—Approximately 2.2 cm.

*Width*.—Approximately 0.5 cm.

*Color*.—Near RHS Green 137C.

*Shape*.—Elliptic.

*Apex*.—Acute.

*Base*.—Obtuse.
*Texture*.—Glabrous.

Peduncle:

*Peduncle length*.—Approximately 17 cm.
*Peduncle diameter*.—Approximately 0.3 cm.
*Aspect*.—Upright with outward curve.
*Color*.—Near RHS Yellow-Green 144A.
*Texture*.—Glabrous.

REPRODUCTIVE ORGANS

*Stamen quantity*.—Approximately 5.
*Filament length*.—Approximately 0.1 cm.
*Anther length*.—Approximately 0.4 cm.
*Anther color*.—Near RHS Yellow-White 158D, tip Greyed-Orange 167B.
*Pollen color*.—Near RHS Yellow 10C.
*Pollen amount*.—Scant to moderate.
*Pistil length*.—Approximately 0.7 cm.
*Style length*.—Approximately 0.2 cm.
*Style color*.—Near RHS Yellow-Green 154D.
*Stigma shape*.—Bulbous with concave depression on uppermost portion.
*Ovary color*.—Near RHS Yellow-Green 150D.
*Stigma color*.—Near RHS Green 138B.

OTHER CHARACTERISTICS

Disease resistance: Neither resistance nor susceptibility to diseases or pests has been observed in this variety.

Temperature tolerance: Tolerates high temperature to at least 35° C. Tolerates low temperatures to −10° C.

Fruit/seed production: Fruit and seed production not observed.

What is claimed is:

1. A new and distinct cultivar of *Viola* plant named 'KERVIODEEP' as herein illustrated and described.

* * * * *